United States Patent
Yu et al.

(10) Patent No.: US 11,970,430 B2
(45) Date of Patent: Apr. 30, 2024

(54) METHOD FOR CO-PRODUCTION OF 1,1-DIFLUOROETHANE AND VINYL CHLORIDE

(71) Applicant: Zhejiang Quhua Fluor-Chemistry Co Ltd, Zhejiang (CN)

(72) Inventors: Huimei Yu, Zhejiang (CN); Jiangyong Hong, Zhejiang (CN); Bo Yang, Zhejiang (CN); Yang Zhao, Zhejiang (CN); Yan Zhang, Zhejiang (CN); Linhui Li, Zhejiang (CN); Yawen Ren, Zhejiang (CN)

(73) Assignee: Zhejiang Quhua Fluor-Chemistry Co Ltd, Zhejiang (CN)

( * ) Notice: Subject to any disclaimer, the term of this patent is extended or adjusted under 35 U.S.C. 154(b) by 360 days.

(21) Appl. No.: 17/627,122

(22) PCT Filed: Jun. 25, 2021

(86) PCT No.: PCT/CN2021/102310
§ 371 (c)(1),
(2) Date: Jan. 13, 2022

(87) PCT Pub. No.: WO2022/105230
PCT Pub. Date: May 27, 2022

(65) Prior Publication Data
US 2023/0265027 A1    Aug. 24, 2023

(30) Foreign Application Priority Data
Nov. 23, 2020    (CN) .......................... 202011319668.4

(51) Int. Cl.
C07C 17/20    (2006.01)
B01J 23/26    (2006.01)
C07C 17/383    (2006.01)

(52) U.S. Cl.
CPC ................ *C07C 17/20* (2013.01); *B01J 23/26* (2013.01); *C07C 17/383* (2013.01)

(58) Field of Classification Search
CPC ....... C07C 17/20; C07C 17/383; C07C 17/25; C07C 19/08; C07C 21/06; B01J 23/26; B01J 23/24; B01J 23/864
See application file for complete search history.

(56) References Cited

U.S. PATENT DOCUMENTS 5,672,788 A    9/1997    Nappa et al.

FOREIGN PATENT DOCUMENTS

| CN | 1141906 | 2/1997 |
|---|---|---|
| CN | 1212678 | 3/1999 |

(Continued)

OTHER PUBLICATIONS

"International Search Report (Form PCT/ISA/210)"of PCT/CN2021/102310, mailed on Sep. 10, 2021, pp. 1-4.

(Continued)

*Primary Examiner* — Jafar F Parsa
(74) *Attorney, Agent, or Firm* — JCIPRNET

(57) ABSTRACT

The present invention provides a method for the co-production of 1,1-difluoroethane and vinyl chloride, including: (a) vaporizing dichloroethane and hydrogen fluoride, and delivering the vaporized dichloroethane and hydrogen fluoride into a reactor for a catalytic reaction under the action of a catalyst to obtain a reaction product; (b) delivering the reaction product into a first rectifying tower for separation to obtain an overhead product from the first rectifying tower and a bottom product from the first rectifying tower; (c) delivering the overhead product from the first rectifying tower into a second rectifying tower for separation to obtain hydrogen chloride and a bottom product from the second rectifying tower; (d) delivering the bottom product from the (Continued)

second rectifying tower into a purifying tower for purification to obtain an overhead product from the purifying tower; (e) simultaneously delivering the overhead product from the purifying tower and a saturated organic solvent into a third rectifying tower for separation to obtain a 1,1-difluoroethane product and a bottom product from the third rectifying tower; and (f) delivering the bottom product from the third rectifying tower into a fourth rectifying tower for separation to obtain a vinyl chloride product and a bottom stream from the fourth rectifying tower. The present invention has the advantages of simple process, high conversion rate, and good product quality.

10 Claims, 1 Drawing Sheet

(56) References Cited

FOREIGN PATENT DOCUMENTS

| CN | 1860089 | 11/2006 |
| CN | 1878738 | 12/2006 |
| CN | 1956940 | 5/2007 |
| CN | 1994985 | 7/2007 |
| CN | 101412654 | 4/2009 |
| CN | 112608213 | 4/2021 |
| CN | 112608216 | 4/2021 |
| WO | 2008107578 | 9/2008 |

OTHER PUBLICATIONS

"Written Opinion of the International Searching Authority (Form PCT/ISA/237)" of PCT/CN2021/102310, mailed on Sep. 10, 2021, pp. 1-5.

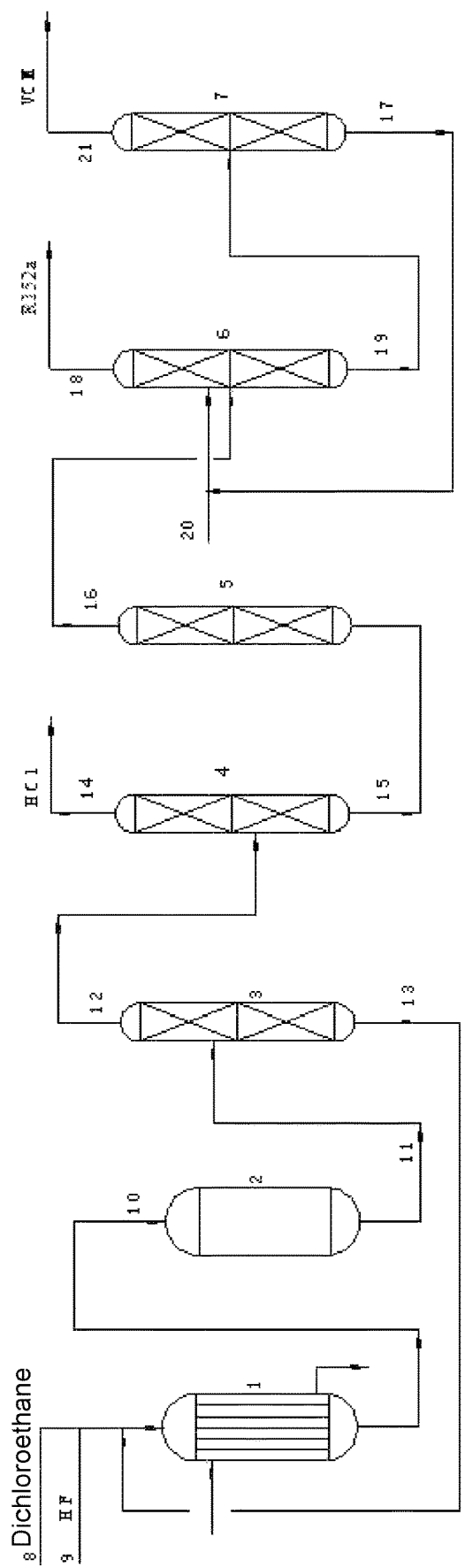

METHOD FOR CO-PRODUCTION OF 1,1-DIFLUOROETHANE AND VINYL CHLORIDE

CROSS-REFERENCE TO RELATED APPLICATION

This application is a 371 of international application of PCT application serial no. PCT/CN2021/102310, filed on Jun. 25, 2021, which claims the priority benefit of China application no. 202011319668.4, filed on Nov. 23, 2020. The entirety of each of the above mentioned patent applications is hereby incorporated by reference herein and made a part of this specification.

TECHNICAL FIELD

The present invention relates to a method for preparing fluorine-containing hydrocarbons, and in particular, relates to a method for the co-production of 1,1-difluoroethane and vinyl chloride.

RELATED ART 1,1-difluoroethane (R152a), with the ozone-depletion potential (ODP) of zero and the global warming potential (GWP) of only 140, is an environment-friendly refrigerant having characteristics such as low boiling point and large refrigeration coefficient. R152a is an important component of mixed refrigerants R401, R405, and R411, and can also act as a single-substance refrigerant. Meanwhile, R152a can be used as a raw material for producing R142b, and the latter is also a raw material for producing polyvinylidene fluoride resins. With good market availability and low price, R152a has been massively produced in China.

At present, conventional synthetic routes for R152a mainly include the following.

(1) Liquid-Phase Fluorination Process with Acetylene as Raw Material

In this process, R152a is prepared by reacting acetylene as a raw material with a hydrofluoric acid in the presence of a catalyst such as boron trifluoride, fluorosulfonic acid, and antimony pentafluoride, with a reaction formula as follows.

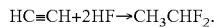

$HC\equiv CH+2HF\rightarrow CH_3CHF_2$.

Its process flow is as follows: the acetylene is purified and dried, and then delivered into a reaction kettle filled with a catalyst (such as fluorosulfonic acid) and hydrofluoric acid for reaction under certain pressure (0.03 MPa-3 MPa) and at certain temperature (20-40° C.) to generate R152a; and after water washing, alkali washing, and deacidification, a gas-phase material is compressed into a liquid-phase material, which is then fractionated and purified to prepare the finished R152a.

For example, Chinese Patent CN1994985A discloses a method for producing R152a in a liquid-phase process with acetylene as a raw material, and a reaction kettle used in this method.

For another example, Chinese Patent CN101412654A provides a method for preparing R152a, in which acetylene and anhydrous hydrofluoric acid as raw materials undergo a fluorination reaction in the presence of a chromium-based fluorination catalyst to prepare the R152a.

This method has the disadvantage that the utilization ratio of the catalyst is low, leading to short reaction period, high unit consumption, and large discharge of residual liquid. Meanwhile, the reaction temperature is difficult to control, since the reaction between the acetylene and the hydrofluoric acid is an exothermic reaction, and released heat also changes with the change of the reaction speed. That is, in a pre-reaction stage with high heat release, cooling instead of heating is needed; and in a post-reaction stage, heating is needed. Therefore, the temperature is difficult to control. If the reaction temperature is slightly lower, the reaction speed is low, and the production capacity of the apparatus is reduced; and if the temperature is slightly higher, the catalyst would lose activity soon, byproducts with high boiling point would be increased, and the consumption of raw materials are increased, both of which are adverse to the production.

(2) Liquid-Phase Fluorination Process with Vinyl Chloride (VCM) as Raw Material

Chinese Patent CN1141906A and Chinese Patent CN1212678A describe methods for producing R152a in a liquid-phase fluorination process with vinyl chloride and anhydrous hydrofluoric acid as raw materials, respectively. In this method, a lot of tar is generated to affect the yield of products, and is also difficult to dispose.

(3) Liquid-Phase Fluorination Process with 1,2-dichloroethane as Raw Material

U.S. Pat. No. 5,672,788 discloses a method for preparing R152a by a two-step liquid-phase reaction. In the first step includes adding at least one of HCl or HF to vinyl chloride to obtain 1,1-dichloroethane or R151a, and in the second step includes converting the 1,1-dichloroethane or R151a into R152a. This method reduces the formation of substances with high boiling point, and slows down the formation of tar, which however cannot be eliminated completely.

Chinese Patent Publication No. CN1860089A discloses a method for producing 1,1-difluoroethane by the liquid-phase fluorination of hydrofluoric acid and 1,2-dichloroethane in the presence of a Lewis acid catalyst and a $FeCl_3$ promoter, where the 1,1-difluoroethane is prepared by fluorinating VCM in a liquid phase in the presence of the catalyst. By employing the liquid-phase fluorination process, this method shows low yield, short catalyst life, and high content of byproduct impurities, which is adverse to the industrial batch production.

However, as starting materials for preparing R152a and in particular for the industrial manufacturing of the same, olefins and alkynes (for example, vinyl chloride) known in the art are prone to tar formation. Meanwhile, in the process of producing R152a by using vinyl chloride, crude products of R152a generally contain 1%-5% of unconverted vinyl chloride, and the unconverted vinyl chloride and R152a would form an azeotrope, and cannot completely separated by common rectification methods. Therefore, in the process of producing R152a by vinyl chloride method, the purification technology of R152a product is also highly concerned by people.

In short, the conventional methods for preparing R152a has the following problems.

(1) A lot of tar is generated.
(2) The azeotrope of vinyl chloride and R152a is difficult to separate, such that the pure product of R152a hardly be obtained.
(3) The catalysts are short in life, many byproducts with high boiling point are generated and the content of impurities is high.

SUMMARY OF INVENTION

In view of the defects in the prior art, the present invention provides a method for the co-production of 1,1-difluoroethane and vinyl chloride, with the advantages of simple process, high conversion rate of raw materials, good activity of catalysts, and good product quality.

To solve the technical problems described above, the present invention is implemented through the following technical solution: a method for the co-production of 1,1-difluoroethane and vinyl chloride. The method includes the following steps.

(a) Dichloroethane and hydrogen fluoride are vaporized by a vaporizer, and the vaporized dichloroethane and hydrogen fluoride are delivered into a reactor for a catalytic reaction under the action of a catalyst to obtain a reaction product.

(b) The reaction product is delivered into a first rectifying tower for separation to obtain an overhead product from the first rectifying tower and a bottom product from the first rectifying tower.

(c) The overhead product from the first rectifying tower is delivered into a second rectifying tower for separation to obtain hydrogen chloride from the top of the second rectifying tower, and a bottom product from the bottom of the second rectifying tower.

(d) The bottom product from the second rectifying tower is delivered into a purifying tower for purification to obtain an overhead product from the purifying tower.

(e) The overhead product from the purifying tower and a saturated organic solvent are simultaneously delivered into a third rectifying tower for separation to obtain a 1,1-difluoroethane product from the top of the third rectifying tower, and a bottom product from the bottom of the third rectifying tower.

(f) The bottom product from the third rectifying tower is delivered into a fourth rectifying tower for separation to obtain a vinyl chloride product and a bottom stream of the fourth rectifying tower.

As a preferred embodiment of the present invention, the catalytic reaction in step (a) occurs at the temperature of 150-300° C., the airspeed of 500-3000 h$^{-1}$ and the pressure of 0.1-1.5 MPa, and a molar ratio of the hydrogen fluoride to the dichloroethane is 3-10:1.

As a preferred embodiment of the present invention, the catalyst in step (a) takes chromium as an active component, and takes one or two selected from IIIA, IIB, VIII, and VIIB-group metallic elements as an auxiliary component or auxiliary components, and a molar ratio of the chromium to the auxiliary component or auxiliary components is 1:0.01-0.2.

As a preferred embodiment of the present invention, in step (d), the purifying tower is filled with a solid deacidification agent and an additive, and a mass ratio of the solid deacidification agent to the additive is 3-5:1.

As a preferred embodiment of the present invention, the solid deacidification agent is a hydroxide selected from IA, IIA, VIIB, VIII, and IIB group elements, and the additive is at least one selected from calcium phosphate, calcium bisulfite, calcium carbonate, calcium bicarbonate, and sodium sulfite.

As a preferred embodiment of the present invention, the saturated organic solvent in step (e) is at least one selected from n-pentane, isopentane, carbon tetrachloride, dichloromethane, and dichloroethane.

As a preferred embodiment of the present invention, a mass ratio of the overhead product from the purifying tower to the saturated organic solvent in step (e) is 1:0.1-10.

As a preferred embodiment of the present invention, the dichloroethane is at least one selected from 1,1-dichloroethane and 1,2-dichloroethane.

As a preferred embodiment of the present invention, the bottom product from the first rectifying tower in step (b) is refluxed to the vaporizer.

As a preferred embodiment of the present invention, the bottom stream from the fourth rectifying tower in step (f) is refluxed to the third rectifying tower.

In the method for the co-production of 1,1-difluoroethane and vinyl chloride according to the present invention, the dichloroethane and hydrogen chloride as raw materials undergo a one-step gas-phase reaction to obtain a reaction product, which is separated and purified to prepare the 1,1-difluoroethane and vinyl chloride products. The method has the advantages of simple process, high conversion rate of raw materials, few byproduct impurities, low energy consumption, as well as good activity and long life of catalysts.

The reaction between the dichloroethane and HF for generating the 1,1-difluoroethane is an exothermic reaction. Meanwhile, as the reaction proceeds, the volume of reaction raw materials is reduced, and the control over the temperature, material ratio, pressure, and reactor airspeed directly affect the conversion rate of the raw materials and the selectivity of the target product R152a.

The reaction temperature has an effect on the conversion rate of the raw materials and the selectivity of the target product R152a. The reaction between the dichloroethane and HF for generating R152a is an exothermic reaction. However, a certain amount of energy has to be provided to reach an activation state so as to allow the reaction to occur. If the temperature is too low, the reaction materials cannot be fully reached the activation state, which would affect the conversion rate of the raw materials and the selectivity of R152a. However, the higher the temperature, the higher the initial activity of the catalyst, and the higher the carbon deposition speed, resulting in the accelerated aging of the catalyst. In this way, the pipelines are easily blocked, and the catalyst is easily deactivated to lead to a shortened life. From tests, the conversion rate of the raw materials increases with the increase of the reaction temperature, and the selectivity of R152a increases and then gradually decreases with the increase of the reaction temperature. Therefore, the control range of the reaction temperature in the present invention is selected to be 150-300° C., preferably 180-280° C.

The reactor airspeed also has an effect on the conversion rate of the raw materials and the selectivity of the target product R152a. The higher the reactor airspeed, the shorter the contact time between the materials and the catalyst. Therefore, as the reactor airspeed increases, the conversion rate of the raw materials and the selectivity of R152a somewhat decrease. However, the lower the reactor airspeed, the smaller the production capacity per unit volume of the reactor, which is adverse to the industrial production. Therefore, the appropriate range of the reactor airspeed in the present invention is 500-3000h$^{-1}$, preferably 1000-2000h$^{-1}$.

The material ratio also has an effect on the conversion rate of the raw materials and the selectivity of the target product R152a. From test results, the higher the molar ratio of HF to dichloroethane, the higher the conversion rate of the raw materials and the selectivity of R152a. Moreover, a large amount of HF can inhibit the carbon deposition on the surface of the catalyst during a reaction process to prolong the life of the catalyst. However, the higher the molar ratio of HF to dichloroethane, the lower the production capacity of the reactor at the same airspeed of the reactor. Therefore, the molar ratio of hydrogen fluoride to dichloroethane in the present invention is 1-10:1, preferably 3-10:1.

In addition, the reaction pressure is also one of the factors affecting the reaction results. If the pressure is too low, the production capacity per unit volume of the reactor is lower, which is not economic; and if the pressure is too high, a strict demand would be made on the material of the apparatus. Therefore, by taking all factors into consideration, the control range of the pressure in the present invention is selected to be 0.1-1.5 MPa, preferably, 0.5-1.0 MPa.

In the present invention, the overhead product from the purifying tower and the saturated organic solvent are simultaneously delivered into the third rectifying tower for separation, which effectively solves the problem that the azeotrope of vinyl chloride and R152a is difficult to separate. To ensure the effect of separating R152a from VCM, the mass ratio of the bottom product from the third rectifying tower to the saturated organic solvent in the present invention is 1:0.1-10, preferably 1:0.4-2.5.

In the traditional deacidification process, water washing and alkali washing are mostly applied to further remove trace acidic substances such as HF, HCl and the like, resulting in a large amount of waste water that needs to be removed through a drying procedure. The present invention employs a purifying process, in which the purifying tower is filled with the solid deacidification agent and the additive. This process substitutes the traditional processes of water washing and alkali washing, and is dispensed with the drying procedure, thereby reducing waste water and energy consumption.

Compared with the prior art, the present invention has the following advantages.
1. The process is simple with high efficiency, which lies in that the present invention can produce two types of products of R152a and VCM at the same time by the same set of apparatus in a gas-phase one-step reaction process; a product ratio can be controlled by changing the reaction conditions to realize intensive production; the operation is simple, the reaction conditions are mild, and the production process is significantly simplified; and the conversion rate per pass of the raw materials is above 90%.
2. The catalyst has good activity and long life, which lies in that the present invention slows down the carbon deposition of the catalyst to effectively prolong the life of the catalyst to above 3 years.
3. The product is good in quality, which lies in that the present invention simultaneously delivers the overhead product from the purifying tower and the saturated organic solvent into the third rectifying tower for separation, which effectively solves the problem that the azeotrope of vinyl chloride and R152a is difficult to separate; and the product purity of R152a is above 99.9%, which meets the requirements of GB/T 19602 for the industrial 1,1-difluoroethane.
4. Environmental protection is achieved, which lies in that the present invention removes trace hydrofluoric acid and hydrogen chloride by using the purifying tower, which substitutes the traditional processes of water washing and alkali washing and is dispensed with the drying procedure, thereby significantly reducing waste water and energy consumption; and the saturated organic solvent is recyclable, emission of three wastes is further reduced.

BRIEF DESCRIPTION OF DRAWINGS

FIGURE is a schematic diagram of a process flow according to the present invention.

As shown in the FIGURE, 1 indicates a vaporizer; 2 indicates a reactor; 3 indicates a first rectifying tower; 4 indicates a second rectifying tower; 5 indicates a purifying tower; 6 indicates a third rectifying tower; 7 indicates a fourth rectifying tower; and 8 to 21 represent process pipelines.

DESCRIPTION OF EMBODIMENTS

A process flow according to the present invention is shown in FIG. 1, in which dichloroethane and HF as raw materials are mixed via pipelines 8 and 9, and then are delivered to a vaporizer 1 for preheating and vaporization; after the preheating and vaporization, a mixed gas is delivered via a pipeline 10 to a reactor 2 filled with a catalyst for reaction, after which a resulting reaction product is delivered to a first rectifying tower 3 via a pipeline 11; a bottom stream containing unreacted raw materials and other heavy components from the bottom of the first rectifying tower 3 is refluxed to the vaporizer 1 via a pipeline 13, and an overhead product from the top of the first rectifying tower is delivered to the second rectifying tower 4 via a pipeline 12 to separate HCl; HCl separated from the top of the second rectifying tower 4 is delivered via a pipeline 14 to other apparatus for later user, and a bottom product from the second rectifying tower 4 is delivered to a purifying tower 5 via a pipeline 15 to remove trace acidic substances such as hydrogen fluoride and hydrogen chloride; the purified overhead product is delivered to a third rectifying tower 6 via a pipeline 16, a saturated organic solvent is simultaneously introduced to the third rectifying tower 6 via a pipeline 20, rectification is conducted to obtain an overhead product of R152a that is produced via a pipeline 18, and a bottom product from the third rectifying tower 6 is delivered to a fourth rectifying tower 7 via a pipeline 19; and a vinyl chloride product is obtained from the top of the fourth rectifying tower 7, and a bottom stream containing the saturated organic solvent is obtained from the bottom of the fourth rectifying tower 7 and is refluxed to the third rectifying tower 6 via a pipeline 17 for cycle use.

The present invention will be further described in detail below in conjunction with specific embodiments, but is not limited to these embodiments only.

The compositions of catalysts in the embodiments are shown in Table 1.

Table 1

| Compositions of catalysts in the embodiments | | | |
| --- | --- | --- | --- |
| No. of catalyst | Active component | Auxiliary component | Molar ratio |
| 1# | Cr | Zn | Cr:Zn = 1:0.01 |
| 2# | Cr | Mn | Cr:Mn = 1:0.05 |
| 3# | Cr | Fe | Cr:Mn = 1:0.2 |
| 4# | Cr | Ni, In | Cr:Ni:In = 1:0.02:0.02 |
| 5# | Cr | Co, Ga | Cr:Co:Ga = 1:0.05:0.05 |

Embodiment 1

1,2-dichloroethane (D12 for short) and HF were mixed and vaporized, and then were delivered to the reactor filled with a catalyst 1 #, the reaction under the action of a catalyst; the purifying tower was filled with $Ca(OH)_2$ as the solid deacidification agent and calcium phosphate as the additive, a mass ratio of $Ca(OH)_2$ to calcium phosphate was 5:1; and the saturated organic agent was dichloroethane ($CH_2Cl_2$), and a mass ratio of an overhead product from the purifying tower to the dichloroethane was 1:0.25. Reaction parameters and organic components at the outlet of the reactor (in percentage by weight, wt %) were shown in Table 2, and the separation results of the third rectifying tower were shown in Table 3.

Embodiment 2

1,1-dichloroethane (D11 for short) and HF were mixed and vaporized, and then were delivered to the reactor filled with a catalyst 2 #, the reaction under the action of a catalyst; the purifying tower was filled with NaOH as the solid deacidification agent and calcium carbonate as the additive, a mass ratio of NaOH to calcium carbonate was 4:1; and the saturated organic agent was carbon tetrachloride ($CCl_4$), and a mass ratio of an overhead product from the purifying tower to the carbon tetrachloride was 1:0.4. Reaction parameters and organic components at the outlet of the reactor (in percentage by weight, wt %) were shown in Table 2, and the separation results of the third rectifying tower were shown in Table 3.

Embodiment 3

1,1-dichloroethane (D11 for short) and HF were mixed and vaporized, and then were delivered to the reactor filled with a catalyst 3 #, the reaction under the action of a catalyst; the purifying tower was filled with $Zn(OH)_2$ as the solid deacidification agent and calcium carbonate as the additive, a mass ratio of $Zn(OH)_2$ to calcium carbonate was 3:1; and the saturated organic agent was a mixture formed from dichloroethane ($CH_2Cl_2$) and carbon tetrachloride ($CCl_4$) at a mass ratio of 1:1, and a total mass ratio of the mixture of an overhead product from the purifying tower to the mixture of dichloroethane ($CH_2Cl_2$) and carbon tetrachloride ($CCl_4$) is 1:1. Reaction parameters and organic components at the outlet of the reactor (in percentage by weight, wt %) were shown in Table 2, and the separation results of the third rectifying tower were shown in Table 3.

Embodiment 4

HF, D11 and D12 were mixed and vaporized, and then were delivered to the reactor filled with a catalyst 4 #, the reaction under the action of a catalyst; the saturated organic agent was D12, and a mass ratio of an overhead product from the purifying tower to D12 was 1:2.3; the purifying tower was filled with $Mg(OH)_2$ as the deacidification agent and calcium bicarbonate as the additive, a mass ratio of $Mg(OH)_2$ to calcium bicarbonate was 4:1. Reaction parameters and organic components at the outlet of the reactor (in percentage by weight, wt %) were shown in Table 2, and the separation results of the third rectifying tower were shown in Table 3.

Embodiment 5

1,2-dichloroethane (D12 for short) and HF were mixed and vaporized, and then were delivered to the reactor filled with a catalyst 5 4, the reaction under the action of a catalyst; the purifying tower was filled with $Ca(OH)_2$ as the solid deacidification agent and calcium bisulfite as the additive, a mass ratio of $Ca(OH)_2$ to calcium bisulfite was 5:1; and the saturated organic agent was D12, and a mass ratio of an overhead product from the purifying tower to D12 was 1:9. Reaction parameters and organic components at the outlet of the reactor (in percentage by weight, wt %) were shown in Table 2, and the separation results of the third rectifying tower were shown in Table 3.

TABLE 2

Reaction parameters and reaction results of Embodiments 1 to 5

| Embodiment | Temperature (° C.) | Airspeed ($h^{-1}$) | Molar ratio | R152a (wt %) | R151a (wt %) | VCM (wt %) | D12 (wt %) | D11 (wt %) | Others (wt %) |
|---|---|---|---|---|---|---|---|---|---|
| 1 | 180 | 2000 | HF/D12 = 1:1 | 67.1 | 3.9 | 20.4 | 8.5 | 0 | 0.1 |
| 2 | 200 | 2200 | HF/D11 = 3:1 | 70.5 | 4.8 | 19.5 | 0 | 5.2 | 0 |
| 3 | 220 | 2500 | HF/D11 = 6:1 | 72.6 | 5.5 | 18.1 | 0 | 3.8 | 0 |
| 4 | 250 | 2500 | HF/D12/D11 = 8:0.5:0.5 | 74.5 | 6.5 | 13.5 | 2.9 | 2.5 | 0.1 |
| 5 | 280 | 2500 | HF/D12 = 10:1 | 82.3 | 4.5 | 10.7 | 2.5 | 0 | 0 |

TABLE 3

Separation results of the third rectifying tower from Embodiments 1 to 5

| Embodiment | Purity (wt %) of overhead R152a product | Components of bottom stream (wt %) |
|---|---|---|
| 1 | 99.90 | VCM: 52.87<br>$CH_2Cl_2$: 45.66<br>R151a: 1.30<br>R152a: 0.17 |
| 2 | 99.92 | VCM: 41.29<br>$CCl_4$: 57.53<br>R151a: 1.06<br>R152a: 0.12 |
| 3 | 99.95 | VCM: 28.17<br>$CH_2Cl_2$: 35.00<br>$CCl_4$: 35.00<br>R151a: 0.78<br>R152a: 0.05 |
| 4 | 99.93 | VCM: 17.75<br>D12: 81.52<br>R151a: 0.66<br>R152a: 0.07 |
| 5 | 99.91 | VCM: 11.21<br>D12: 88.19<br>R151a: 0.52<br>R152a: 0.08 |

What is claimed is:

1. A method for the co-production of 1,1-difluoroethane and vinyl chloride, comprising the following steps:
   (a) vaporizing dichloroethane and hydrogen fluoride by a vaporizer, and delivering the vaporized dichloroethane and hydrogen fluoride into a reactor for a catalytic reaction under the action of a catalyst to obtain a reaction product;
   (b) delivering the reaction product into a first rectifying tower for separation to obtain an overhead product from the first rectifying tower and a bottom product from the first rectifying tower;

(c) delivering the overhead product from the first rectifying tower into a second rectifying tower for separation to obtain hydrogen chloride from the top of the second rectifying tower and a bottom product from the bottom of the second rectifying tower;

(d) delivering the bottom product from the second rectifying tower into a purifying tower for purification to obtain an overhead product from the purifying tower;

(e) simultaneously delivering the overhead product from the purifying tower and a saturated organic solvent into a third rectifying tower for separation to obtain a 1,1-difluoroethane product from the top of the third rectifying tower and a bottom product from the bottom of the third rectifying tower; and (f) delivering the bottom product from the third rectifying tower into a fourth rectifying tower for separation to obtain a vinyl chloride product and a bottom stream from the fourth rectifying tower.

2. The method for the co-production of 1,1-difluoroethane and vinyl chloride according to claim 1, wherein the catalytic reaction in the step (a) occurs at a temperature of 150-300° C., an airspeed of 500-3000 $h^{-1}$, a pressure of 0.1-1.5 MPa, and a molar ratio of the hydrogen fluoride to the dichloroethane is 3-10:1.

3. The method for the co-production of 1,1-difluoroethane and vinyl chloride according to claim 1, wherein the catalyst in the step (a) takes chromium as an active component, and takes one or two selected from IIIA, IIB, VIII, and VIIB group metallic elements as an auxiliary component or auxiliary components, and a molar ratio of the chromium to the auxiliary component or auxiliary components is 1:0.01-0.2.

4. The method for the co-production of 1,1-difluoroethane and vinyl chloride according to claim 1, wherein in the step (d), the purifying tower is filled with a solid deacidification agent and an additive, and a mass ratio of the solid deacidification agent to the additive is 3-5:1.

5. The method for the co-production of 1,1-difluoroethane and vinyl chloride according to claim 4, wherein the solid deacidification agent is a hydroxide selected from IA, IIA, VIIB, VIII, and IIB group elements, and the additive is at least one selected from calcium phosphate, calcium bisulfite, calcium carbonate, calcium bicarbonate, and sodium sulfite.

6. The method for the co-production of 1,1-difluoroethane and vinyl chloride according to claim 1, wherein the saturated organic solvent in the step (e) is at least one selected from n-pentane, isopentane, carbon tetrachloride, dichloromethane, and dichloroethane.

7. The method for the co-production of 1,1-difluoroethane and vinyl chloride according to claim 1, wherein a mass ratio of the overhead product from the purifying tower to the saturated organic solvent in the step (e), is 1:0.1-10.

8. The method for the co-production of 1,1-difluoroethane and vinyl chloride according to claim 1, wherein the dichloroethane is at least one selected from 1,1-dichloroethane and 1,2-dichloroethane.

9. The method for the co-production of 1,1-difluoroethane and vinyl chloride according to claim 1, wherein the bottom product from the first rectifying tower in the step (b) is refluxed to the vaporizer.

10. The method for the co-production of 1,1-difluoroethane and vinyl chloride according to claim 1, wherein the bottom stream from the fourth rectifying tower in the step (f) is refluxed to the third rectifying tower.

* * * * *